(12) United States Patent
Won et al.

(10) Patent No.: US 7,138,132 B2
(45) Date of Patent: *Nov. 21, 2006

(54) HYDROGEL ENTRAPPING THERAPEUTIC AGENT AND STENT WITH COATING COMPRISING THIS

(75) Inventors: Chee-Youb Won, Livingston, NJ (US); Yeli Zhang, Somerville, NJ (US); Chih-Chang Chu, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 51 days.

This patent is subject to a terminal disclaimer.

(21) Appl. No.: 11/037,011

(22) Filed: Jan. 19, 2005

(65) Prior Publication Data

US 2005/0129734 A1   Jun. 16, 2005

Related U.S. Application Data

(63) Continuation of application No. 10/762,256, filed on Jan. 23, 2004, now Pat. No. 6,905,700, which is a continuation of application No. 10/143,572, filed on May 13, 2002, now Pat. No. 6,716,445, which is a continuation-in-part of application No. 09/531,451, filed on Mar. 20, 2000, now Pat. No. 6,388,047.

(60) Provisional application No. 60/128,803, filed on Apr. 12, 1999.

(51) Int. Cl.
*C09D 4/00* (2006.01)
*A61L 25/00* (2006.01)
*A61L 27/00* (2006.01)
*A61L 29/00* (2006.01)

(52) U.S. Cl. ............... 424/426; 424/484; 424/486; 424/487; 424/488; 523/105; 525/937

(58) Field of Classification Search ............... 424/426, 424/484, 486, 487, 488; 523/105; 525/937
See application file for complete search history.

(56) References Cited

U.S. PATENT DOCUMENTS

| | | | |
|---|---|---|---|
| 4,002,173 A | 1/1977 | Manning et al. | 128/296 |
| 4,032,488 A | 6/1977 | Hokkoku et al. | 260/17.4 |
| 4,657,553 A | 4/1987 | Taylor | 623/66 |
| 5,278,201 A | 1/1994 | Dunn et al. | 523/113 |
| 5,278,202 A | 1/1994 | Dunn et al. | 523/113 |
| 5,410,016 A | 4/1995 | Hubbell et al. | 528/354 |
| 5,488,102 A | 1/1996 | Vetter | 536/32 |
| 5,514,379 A | 5/1996 | Weissleder et al. | 424/426 |
| 5,514,380 A | 5/1996 | Song et al. | 424/426 |
| 5,540,929 A | 7/1996 | Narayan et al. | 424/422 |
| 5,563,056 A | 10/1996 | Swan et al. | 435/180 |
| 5,567,435 A | 10/1996 | Hubbell et al. | 424/426 |
| 5,571,882 A | 11/1996 | Vetter | 526/238.2 |
| 5,573,934 A | 11/1996 | Hubbell et al. | 435/177 |
| 5,607,686 A | 3/1997 | Totakura et al. | 424/426 |
| 5,616,671 A | 4/1997 | Narayan et al. | 527/300 |
| 5,626,863 A | 5/1997 | Hubbell et al. | 424/426 |
| 5,644,049 A | 7/1997 | Giusti et al. | 526/53 |
| 5,700,848 A | 12/1997 | Soon-Shiong et al. | 522/7 |
| 5,854,382 A | 12/1998 | Loomis | 528/354 |
| 5,900,245 A | 5/1999 | Sawhney et al. | 424/426 |
| 6,201,065 B1 | 3/2001 | Pathak et al. | 525/90 |
| 6,368,356 B1 | 4/2002 | Zhong et al. | 623/23.75 |
| 6,388,047 B1 * | 5/2002 | Won et al. | 528/354 |
| 6,583,219 B1 * | 6/2003 | Won et al. | 525/54.2 |
| 6,592,895 B1 * | 7/2003 | Lang et al. | 424/457 |
| 6,709,668 B1 * | 3/2004 | Won et al. | 424/426 |
| 6,716,445 B1 * | 4/2004 | Won et al. | 424/426 |
| 6,905,700 B1 * | 6/2005 | Won et al. | 424/426 |
| 6,916,857 B1 * | 7/2005 | Won et al. | 523/105 |

FOREIGN PATENT DOCUMENTS

| | | |
|---|---|---|
| SU | 729197 | 4/1980 |
| WO | WO 96/13511 | 5/1996 |
| WO | WO 00/12619 | 3/2000 |
| WO | WO 02/18477 | 3/2002 |

OTHER PUBLICATIONS

Aso, Y., et al., "Determination of the Diffusion Coefficient of Insulin and Lysozyme in Crosslinked Dextran Hydrogels . . . ", Chem. Pharm. Bull., 46 (11), p. 1836-1839, (1998).

Kurisawa, M., et al., "Modulated degradation of dextran hydrogels grafted with poly(N-isopropyl-acrylamide-co-N,N-dimethylacrylamide . . . ", Macromol. Chem. Phys., 199, p. 2613-2618 (1998).

(Continued)

*Primary Examiner*—Nathan M. Nutter
(74) *Attorney, Agent, or Firm*—Bacon & Thomas, PLLC (57) ABSTRACT

A hydrogel forming system which comprises a hydrophobic macromer with unsaturated group terminated ends and a hydrophilic polymer which is a polysaccharide containing hydroxy groups which are reacted with unsaturated group introducing compound, is convertible by free radical polymerization to form a hydrogel containing a three dimensional crosslinked polymer network containing hydrophobic and hydrophilic components. Agent can be entrapped in the polymer network, e.g., drugs, macromolecules or synthetic or natural polymers, for controlled release therefrom. In one embodiment, a vascular stent is coated with hydrogel with therapeutic agent entrapped therein.

3 Claims, 3 Drawing Sheets

OTHER PUBLICATIONS

Pillay, V., et al., "Ionotropic gelation: encapsulation of indomethacin in calcium alginate gel discs", J. Microencapsulation, vol. 15, No. 2, p. 215-226, 1998.

van Dijk-Wolthuis, W.N.E., et al., "A new class of polymerizable dextrans with hydrolyzable groups: hydroxyethyl . . . ", Polymer, vol. 38, No. 25, p. 6235-6242, 1997.

Kurisawa, M., et al., "Double-stimuli-responsive degradation of hydrogels consisting of oligopeptide-terminated poly(ethylene gylcol) . . . ", J. Biomater. Sci, Polymer Edn., vol. 8, No. 9, p. 691-708 (1997).

Zhang, Y., et al., "Synthesis and Characterization of Biodegradable Network Hydrogels Having Both Hydrophobic . . . ", J. Polymer Sci.: Part A: Polymer Chem., vol. 37, p. 4554-4569 (1999).

* cited by examiner

HYDROGEL ENTRAPPING THERAPEUTIC AGENT AND STENT WITH COATING COMPRISING THIS

CROSS-REFERENCE TO RELATED APPLICATION

This application is a of U.S. patent application Ser. No. 10/762,256, filed Jan. 23, 2004, and now U.S. Pat. No. 6,905,700, which in turn is a continuation of U.S. patent application Ser. No. 10/143,572, filed May 13, 2002, and now U.S. Pat. No. 6,716,445, which in turn is a continuation-in-part of U.S. patent application Ser. No. 09/531,451, filed Mar. 20, 2000, and now U.S. Pat. No. 6,388,047, which claims the benefit of U.S. Provisional Application No. 60/128,803, filed Apr. 12, 1999.

TECHNICAL FIELD

This invention relates to a hydrogel-forming system with hydrophobic and hydrophilic components which forms a hydrogel with a crosslinked polymer network structure, hydrogels therefrom entrapping therapeutic agents and vascular stents with coating comprising said hydrogel entrapping therapeutic agent.

BACKGROUND OF THE INVENTION

Up until recently, hydrogels have been based only on hydrophilic components. The need for a new class of hydrogels having both hydrophilic and hydrophobic segments has been highlighted by the increasingly available new therapeutic proteins, peptides and oligonucleotides that are mainly of a hydrophobic nature because it is difficult to homogeneously disperse hydrophobic drugs or hydrophobic bioactive molecules within a totally hydrophilic polymer hydrogel to achieve predictable drug release profiles. Moreover, apart from the need to more effectively handle hydrophobic drugs, hydrogels with hydrophobic and hydrophilic components have the advantages over totally hydrophilic-based hydrogels in maintaining structural integrity for relatively longer periods of time and in mechanical strength.

Despite the need for and advantages of hydrogels having both hydrophilic and hydrophobic components, there are only a few reported studies on these. All these studies rely on either synthesis of copolymers from appropriate monomers without crosslinking or rely on the physical blending of hydrophobic and hydrophilic polymers. The synthesis of copolymer involved copolymerization of polylactide oligomer and polyethylene glycol and did not provide a hydrogel with a crosslinked polymer network or hydrophobic property. The method of physical blending has the major flaw of poor integration between hydrophilic and hydrophobic components, i.e., lack of uniformity throughout the composition.

SUMMARY OF THE INVENTION

The invention herein provides a hydrogel with both hydrophobic and hydrophilic components without relying on the copolymer approach or physical blending but instead relies on hydrophobic and hydrophilic components which are convertible into a one phase crosslinked polymer network structure by free radical polymerization.

In one embodiment herein, denoted the first embodiment, the invention is directed to a hydrogel-forming system which comprises from 0.01 to 99.99% by weight of (A) a hydrophobic macromer with unsaturated group, e.g., vinyl group, terminated ends and from 99.99 to 0.01% by weight of (B) a hydrophilic polymer which is a polysaccharide containing hydroxyl groups which are reacted with unsaturated group, e.g., vinyl group, introducing compound; wherein the total of the percentages of (A) and (B) is 100%.

Preferably, the hydrophobic macromer is biodegradable and very preferably is prepared by reacting diol obtained by converting hydroxy of terminal carboxylic acid group of poly(lactic acid) to aminoethanol group, with unsaturated group introducing compound.

Preferably, the hydrophilic polymer is dextran wherein one or more hydroxyls in a glucose unit of the dextran is (are) reacted with unsaturated group introducing compound.

In one case, the hydrophilic polymer can be dextran-maleic acid monoester as described in WO 00/12619 which is incorporated herein by reference.

In another embodiment, denoted the second embodiment, a hydrogel, preferably a biodegradable hydrogel, is formed by the free radical polymerization, preferably by photo-crosslinking, of the hydrogel-forming system of the embodiment described above, which has a three dimensional crosslinked polymer network structure. In one alternative of this embodiment, a drug of weight average molecular weight ranging from 200 to 1,000, as exemplified by indomethacin, is entrapped in the three dimensional crosslinked polymer network for controlled release therefrom. In another alternative of this embodiment, a macromolecule of weight average molecular weight ranging from 1,000 to 100,000, e.g., a polypeptide, as exemplified by insulin, is entrapped in the three dimensional crosslinked polymer network for controlled release therefrom. In still another alternative of this embodiment, a synthetic or natural polymer, e.g., of weight average molecular weight ranging from 10,000 to 500,000, is entrapped in the three dimensional crosslinked polymer network for controlled release therefrom.

One variation of the second embodiment is directed to a hydrogel which has a three dimensional crosslinked polymer network containing hydrophobic and hydrophilic components having entrapped in the three dimensional structure bioactive agent selected from the group consisting of drugs or biologics of weight average molecular weight ranging from 200 to 1,000, macromolecules of weight average molecular weight ranging from 1,000 to 100,000 and synthetic or natural polymers of weight average molecular weight ranging from 10,000 to 500,000, said hydrogel being formed by the free radical polymerization of a hydrogel-forming system which comprises from 0.01 to 99.99% by weight of (A) a hydrophobic macromer with unsaturated group terminated ends, and from 99.99 to 0.01% by weight of (B) a hydrophilic polymer which is a polysaccharide containing hydroxy groups which are reacted with unsaturated group introducing compound, the total of the percentages of (A) and (B) being 100%. In a preferred case, the agent is a therapeutic agent for treating, postponing or preventing disorder selected front the group consisting of coronary artery disease, inflammation, restenosis and stent rejection and is present in a therapeutically effective amount.

In another embodiment, denoted the third embodiment, a cardiac stent contains a coating comprising the hydrogel containing entrapped agent as described in the paragraph directly above this one.

The term "hydrogel" is used herein to mean a polymeric material which exhibits the ability to swell in water and to retain a significant portion of water within its structure without dissolving.

A biodegradable hydrogel herein is a hydrogel formed from a hydrogel forming system containing at least one biodegradable component, i.e., component which is degraded by water and/or by enzymes found in nature.

The term "crosslinked polymer network structure" is used herein to mean an interconnected structure where crosslinks are formed between hydrophobic molecules, between hydrophilic molecules and between hydrophobic molecules and hydrophilic molecules.

The term "photocrosslinking" is used herein to mean causing vinyl bonds to break and form crosslinks by the application of radiant energy.

The term "macromer" is used herein to mean monomer having a weight average molecular weight ranging from 500 to 80,000.

The term "unsaturated group introducing compound" is used herein to mean compound that reacts with hydroxyl group and provides a pendant or end group containing an unsaturated group, e.g., a pendant group with a vinyl group at its end.

The weight average molecular weights herein are determined by gel permeation chromatography.

The number average molecular weights herein are determined by gel permeation chromatography.

DETAILED DESCRIPTION

We turn now to the hydrogel-forming system which comprises from 0.01 to 99.99%, for example, from 5 to 95%, by weight of (A) a hydrophobic macromer with unsaturated group terminated ends, and from 99.99 to 0.01%, for example, from 95% to 5%, by weight of (B) a hydrophilic polymer which is a polysaccharide containing hydroxy groups which are reacted with unsaturated group introducing compound, wherein the total of the percentages of (A) and (B) is 100%.

We turn to the hydrophobic macromer (A). Such macromer is readily obtained by converting the end groups of a starting material macromer to group with terminal hydroxyl group if such are not already present as end groups, i.e., to provide a diol, and reacting the terminal hydroxyls with unsaturated group introducing compound to provide terminal unsaturated groups, e.g., vinyl groups, on the macromer. The starting material macromer preferably has a weight average molecular weight ranging up from 500 to 20,000. The starting material macromer is preferably the aliphatic polyester poly(lactic acid) having a weight average molecular weight ranging from 600 to 8,000, e.g., 600 to 1,000 or 6,500 to 8,000. The poly(lactic acid) is very preferably poly-D-,L-lactic acid (sometimes denoted PDLLA). Poly-D,L-lactic acid has widely been used as a biodegradable hydrophobic polymeric material due to its combination of biodegradability, biocompatibility, and adequate mechanical strength. The degradation of poly-D,L-lactic acid is well understood and the degradation products are natural metabolites that can be readily eliminated by the human body. Other starting material macromers can be, for example, other aliphatic polyesters, for example, poly(glycolic acid), poly(ε-caprolactone), poly(glycolide-co-lactide), poly(lactide-ε-caprolactone), polycaprolactone diols (e.g., with $M_n$ equal to 530, 1250 or 2000), polycaprolactone triols (e.g., with $M_n$ equal to 300 or 900), or any synthetic biodegradable macromer having one carboxyl end group and one hydroxyl end group or carboxyl groups at both ends or hydroxyl groups at both ends.

Terminal carboxyl groups of starting material macromers can be converted to group with terminal hydroxyl by reacting the hydroxy of the terminal carboxyl with 2-aminoethanol in the presence of 1,3-dicyclohexylcarbodiimide (DCC) as a dehydrating agent and 1-hydroxylbenzotriazole (HOBT) as an auxiliary nucleophile to improve reaction rates and suppress any side reactions.

Poly(lactic acid) starting material can be converted to diol, for example, by dissolving poly(lactic acid) in tetrahydrofuran under a nitrogen purge, cooling to 0° C., adding HOBT and DCC, stirring for 0.5 to 2 hours, allowing to reach room temperature, then adding 2-aminoethanol, and stirring at room temperature for 0.5 to 24 hours. Byproduct cyclohexylurea salt precipitates and is filtered out. The amount of 2-aminoethanol is the most significant variable and preferably the mole ratio of 2-aminoethanol to poly(lactic acid) ranges from 1:1 to 15:1, depending on the molecular weight of the poly(lactic acid). The mole ratio of 2-aminoethanol to poly(lactic acid) more preferably should be at least 1.1:1, as for mole ratios less than this, there was incomplete conversion of carboxyl end group to hydroxyl group. Preferably, the mole ratio of DCC to poly(lactic acid) ranges from 1:1 to 15:1, depending on the molecular weight of the poly(lactic acid), and preferably, the mole ratio of HOBT to poly(lactic acid) ranges from 1:1 to 15:1, depending on the molecular weight of the poly(lactic acid). When these mole ratios are less than 1:1 and the poly(lactic acid) has a weight average molecular weight of 600 to 1,000, the conversion of carboxyl chain end group to hydroxyl group is incomplete even if reaction time is extended. The reason for the 0° C. initial temperature is to provide a mild reaction and to reduce or eliminate side reactions. The time at 0° C. preferably ranges from 0.5 to 1 hours. The time at room temperature preferably ranges from 0.5 to 1 hours as the conversion is completed during the first hour of reaction. Optimum reaction conditions for poly(lactic acid) starting material of weight average molecular weight of 800 were found to be: mole ratio of DCC to poly(lactic acid) of 1:1, mole ratio of HOBT to poly(lactic acid) of 1:1, reaction at 0° C. for 0.5 hours, after returning to room temperature addition of 1.1 moles 2-aminoethanol per mole of poly(lactic acid) and reaction for 0.5 hours; for these optimum conditions, the conversion of terminal carboxyl to hydroxyl was 100% and the yield was more than 95%.

We turn now to the reaction of diol with unsaturated group introducing compound to provide hydrophobic polymer with unsaturated end groups.

The unsaturated group introducing compound can be, for example, acryloyl chloride, methacryloyl chloride, acrylic acid, methacrylic acid, or isocyanate having unsaturated, e.g., vinyl, group at one end of the molecule, e.g., allyl isocyanate or isocyanatoethyl methacrylate.

We turn now to where the vinyl group introducing compound is acryloyl chloride. The reaction is carried out in a solvent in the presence of an acid acceptor. For diol obtained from poly(lactic acid), the reaction can be carried out in tetrahydrofuran (THF) as the reaction solvent and triethylamine is a suitable acid acceptor. Preferably, the triethylamine is added to solution of diol in THF at 0° C. and then the acryloyl chloride is added and stirring is continued first at 0° C. and then at room temperature. The diethanolamine hydrochloride byproduct can be removed by filtering. The mole ratio of triethylamine to diol preferably ranges from 3:1 to 15:1. The mole ratio of acryloyl chloride to diol preferably ranges from 3:1 to 15:1. The time at 0° C. after acryloyl chloride addition preferably ranges from 2 to 4 hours. The time at room temperature preferably ranges from 10 to 48 hours. High ratios of acryloyl chloride to diol (e.g., 8:1) and triethylamine to diol (e.g., 8:1) can lead to cleavage of polymer backbone when the poly(lactic acid) has a weight average molecular weight of 600 to 1,000. Reaction time increase at room temperature from 3 hours to 21 hours led to higher conversion. The optimal reaction conditions where the starting material was poly(lactic acid) having a weight average molecular weight of 800, were found to be 4 moles of acryloyl chloride per mole of diol, 4 moles triethylamine per mole of diol, reaction at 0° C. for 3 hours and subsequent reaction at room temperature for 18 hours; these optimal reaction conditions produced a yield of about 90%. The 0° C. reaction period negates the violent reaction of acryloyl chloride and triethylamine that would occur at higher initial reaction temperatures.

A reaction scheme for synthesis of vinyl terminated hydrophobic macromer A from poly-D,L-lactic acid is set forth below where n ranges, for example, from 8 to 120.

We turn now to where diol is reacted with unsaturated group introducing compound which is isocyanate having vinyl group at one end of the molecule. The isocyanate can be, for example, allyl isocyanate or isocyanatoethyl methacrylate. For diol obtained from poly(lactic acid), reaction with allyl isocyanate can be carried out, for example, using a molar ratio of allyl isocyanate to diol ranging from 1:1 to 1:2, and a temperature ranging from room temperature to 50° C. in polar solvent, e.g., dimethyl sulfoxide, in the presence of organotin catalyst, e.g., dibutyltin dilaurate. There is no byproduct.

We turn now to the hydrophilic polymer (B).

The hydrophilic polymer (B) is a polysaccharide derivative.

The polysaccharides useful for preparing (B) have hydroxy function pendant groups. They include, for example, dextran, inulin, starch, cellulose, pullan, levan, mannan, chitin, xylan, pectin, glucuronan, laminarin, galactomannan, amylose, amylopectin, and phytophtoorglucans. They have multiple hydroxy functional groups which permit the production of a three dimensional network. The named polysaccharides are inexpensive.

We turn now to dextran which is the preferred polysaccharide starting material. Dextran is one of the most abundant naturally occurring biodegradable polymers. It is susceptible to enzymatic digestion in the body. It consists mainly of (1→6) α-D-glucoside linkages with about 5–10% of (1→3) α-linked branching. It contains three hydroxyl groups per glucose repeating unit and therefore mediates formation of a crosslinked polymer network. Preferably, the dextran starting material has a weight average molecular weight ranging from 40,000 to 80,000.

We turn now to the reaction of polysaccharide hydroxy groups with unsaturated group introducing compound.

The unsaturated group introducing compound can be, for example, acryloyl chloride, methacryloyl chloride, acrylic acid, methacrylic acid, or isocyanate having unsaturated, e.g., vinyl, group at one end of the molecule, e.g., allyl isocyanate or isocyanatoethyl methacrylate.

Where acryloyl chloride is the unsaturated group introducing compound, the hydrophilic polymer (B) can be obtained by forming a homogeneous solution of polysaccharide starting material, then adding an acid acceptor, and then adding acryloyl chloride and reacting to form the polymer (B). Where the polysaccharide starting material is dextran, the dextran can be dissolved in LiCl/N,N-dimethylformamide (DMF) (the LiCl functions to make the DMF solvent more polar), and solution can be obtained by adding the dextran to the solvent and raising the temperature, for example, to 120° C., over, for example, two hours, until a homogenous solution is formed, and the solution is preferably cooled to room temperature before acid acceptor is added, and the acid acceptor can be pyridine, and the acryloyl chloride is desirably added to the reaction mixture in the form of a DMF solution, and the molar ratios of acryloyl chloride to anhydroglucose residue unit of the dextran and of pyridine to anhydroglucose residue unit of the dextran are preferably the same and can range, for example, from 1:1 to 6:1, preferably from 2:1 to 3:1, and the reaction is preferably carried out at room temperature over a reaction time ranging, for example, from 3 to 24 hours, very preferably from 3 to 6 hours. The degree of conversion of hydroxyl group to vinyl terminated group increases as molar ratios of acryloyl chloride and pyridine are increased within the aforementioned preferred range and as reaction time increases but when said molar ratios are increased further, e.g., to 6:1, said degree of conversion decreases. Degrees of substitution (number of vinyl groups per 100 anhydroglucose units) ranging from 1.50 to 4.80, e.g., about 3.70, have been obtained. A reaction scheme for synthesis of hydrophilic polymer (B) from dextran using acryloyl chloride as the unsaturated group introducing compound is set forth below where m ranges, for example, from 260 to 430.

The byproduct in the above reaction is pyridine hydrochloride. Compound (5) in the above reaction scheme may be referred to herein as dextran acrylate.

Where isocyanate having vinyl group at one end of the molecule is the unsaturated group introducing compound, the hydrophilic polymer (B) can be obtained by dissolving the polysaccharide starting material in a solvent for both said polysaccharide starting material and said isocyanate and adding any catalyst, and then adding the isocyanate, and then stirring at an effective reaction temperature for an effective reaction time to cause reaction. Where the polysaccharide starting material is dextran, and the isocyanate is allyl isocyanate, the solvent can be, for example, dimethyl sulfoxide (DMSO) and suitable catalyst is dibutyltin dilaurate and the mole ratio of the dibutyltin dilaurate catalyst to anhydroglucose residue unit of dextran can range, for example, from 0.05:1 to 0.1:1, and the mole ratio of allyl isocyanate to anhydroglucose unit of dextran can range, for example, from 0.25:1 to 1:1 and the reaction temperature can range, for example, from room temperature to 60° C. and reaction time can range, for example, from 2 to 8 hours. Increase in each of the parameters (i.e., mole ratio of dibutyltin dilaurate catalyst to anhydroglucose residue unit of dextran, mole ratio of allyl isocyanate to anhydroglucose residue unit of dextran, reaction time and reaction temperature) were found to increase degree of substitution, i.e., the number of allyl isocyanate groups per 100 anhydroglucose units. Degrees of substitution ranging from about 1 to about 15 have been obtained. A reaction scheme for synthesis of hydrophilic polymer (B) from dextran using allyl isocyanate as the unsaturated group introducing compound is set forth below where m ranges, for example, from 260 to 430.

$$R = \underset{\text{(3)}}{-\overset{O}{\overset{\|}{C}}-\overset{H}{\overset{|}{N}}-CH_2-CH=CH_2 \text{ or } H}$$

There is no byproduct in the above reaction. The product of the above reaction may be referred to herein as dex-AI.

The percentages of (A) and (B), the molecular weight of the hydrophobic macromer, the molecular weight of the hydrophilic polymer, and the degree of substitution in the hydrophilic polymer, are variables affecting hydrophobicity/hydrophilicity, mechanical, swelling ratio and biodegradation properties of the hydrogel prepared from the hydrogel-forming systems herein. The "swelling ratio" is defined as follows $$\text{Swelling ratio (\%)} = \frac{W_t - W_0}{W_0} \times 100$$

where $W_t$ is the weight of the hydrogel at time t and $W_0$ is the initial weight of the hydrogel before swelling. Data for swelling ratio is obtained by immersing a known weight of dry hydrogel in a vial containing 15 ml liquid, removing swollen hydrogel from the liquid at regular time intervals, wiping off surface water and weighing, until equilibrium is obtained.

As indicated above, the amounts of (A) and (B) respectively range from 0.01 to 99.99% by weight and 99.99 to 0.01% by weight with the total of the percentages of (A) and (B) being 100. As indicated above, the weight average molecular weight of poly-D,L-lactic acid preferably ranges from 600 to 1,000 or 6,500 to 8,000. As indicated above, dextran starting material has a weight average molecular weight ranging from about 40,000 to 80,000. Degrees of substitution (vinyl group containing substituent per 100 anhydroglucose units) in the polymer (B) have been obtained ranging from about 1 to about 15.

Decreasing the percentage of (B) and increasing the percentage of (A) increases hydrophobicity (and compatibility with hydrophobic agents and milieus) and decreases swelling ratio (with the largest percentage decrease in swelling ratio being found in decreasing the percentage of (B) from 80% to 60% and increasing the percentage of (A) from 20% to 40%). Increasing the percentage of (B) and decreasing the percentage of (A) increases hydrophilicity and compatibility of hydrogel with hydrophilic agents and milieus. Increasing the percentage of (A) improved mechanical properties in the hydrogels formed from the hydrogel-forming systems. Increasing the molecular weight of (A) increases hydrophobicity and mechanical properties, increases swelling ratio where the percentage of A or B is high and causes increase in biodegradation time for formed hydrogel. Increase in the molecular weight of (B) decreases hydrophobicity, decreases swelling ratio, causes increase in mechanical properties, and where (B) is a dextran derivative increases time for degradation by dextranase, in formed hydrogel. Increase in degree of substitution in hydrophilic polymer decreases hydrophilicity and swelling ratio (in higher weight percentage dextran derivative compositions), increases mechanical property and increases degradation time, in formed hydrogel.

We turn now to the embodiment of hydrogel formed by free radical polymerization of the hydrogel-forming system herein, where the hydrogel formed has a three dimensional crosslinked polymer network structure. The free radical polymerization is preferably photopolymerization which can be carried out by dissolving the hydrogel-forming system herein, i.e., dissolving both components (A) and (B) in selected amounts within the ranges specified above, then adding photoinitiator, e.g., from 1 to 5% by weight photoinitiator based on the total weights of the polymers (A) and (B), then forming a film of the resulting admixture of thickness of 0.5 to 2 mm and then subjecting the film to UV irradiation, e.g., using a low-intensity, portable long wave length ultra violet lamp (LWUV lamp) at room temperature until a nontacky hydrogel is obtained. Completion of photopolymerization can be obtained in a time ranging from 10 minutes to 3 hours even in the presence of oxygen. For a hydrogel-forming system of macromer (A) obtained from poly-D,L-lactic acid starting material and of polymer (B) which is dextran diacrylate, hydrogel can be formed by dissolving (A) and (B) in amounts to provide percentages within the ranges set forth above in DMSO to provide a concentration of total of (A) and (B) in the DMSO ranging from 30 to 50% w/v and a homogeneous solution, then adding, for example, 2,2-dimethoxy 2-phenyl acetophenone, as the photoinitiator, e.g., in an amount ranging from 1 to 5% w/w (on the basis of the total weight of (A) and (B)), then transferring the mixture to a hydrophobic plate to form a film thereon and then irradiating with UV irradiation for 1 to 3 hours; the color of the hydrogel changed from optically transparent to light yellow transparent as the polymer (A) compound was incorporated and the yellow intensity increased with increase in polymer (A) incorporation. For a hydrogel-forming system of macromer (A) obtained from poly-D,L-lactic acid starting material and of polymer (B) which is dex-Al, the components can be dissolved in N,N-dimethylformamide to provide a concentration ranging from 30 to 50% (w/v) and then proceeding as described for the hydrogel-forming system involving macromer (A) obtained from poly-D,L-lactic acid and polymer (B) which is dextran diacrylate. It has been found that shorter UV cross-linking times, e.g., 0.5 to 1 hours, lead to a higher swelling ratios. It is preferred that the resulting hydrogels be subjected to extraction to remove unreacted (non-crosslinked) components and solvent, and that then the hydrogels be dried, very preferably, so they are dry to the touch. In general, such extraction increases the swelling ratio of the formed hydrogel.

Analysis has shown that the hydrogels formed herein contain a crosslinked polymer network structure.

The hydrogel formed herein can chemically incorporate a bioactive agent which reacts with either or both of the components of the hydrogel-forming system; this can be accomplished by reacting the bioactive agent with one or both of the components of the hydrogel-forming system herein.

Bioactive agents which are not reactive with components of the hydrogel-forming system herein can be physically entrapped within the hydrogel or physically encapsulated within the hydrogel by including them in the reaction mixture subjected to photocrosslinking so that the photocrosslinking causes formation of hydrogel with bioactive agent entrapped therein or encapsulated thereby.

A wide range of swelling behavior of the PDLLA acrylate/dex-AI hydrogels of the invention herein has been demonstrated over a range of pH buffer media (from pH 3 to 10); generally a biphasic swelling pattern was found for all hydrogels, i.e., an initial rapid swelling phase and a second gradual swelling phase.

By varying the parameters as discussed above, to vary hydrophobicity/hydrophilicity, mechanical, swelling ratio and biodegradation properties, the hydrogel-forming system herein can be tailored to produce hydrogels for drug control release devices, for wound coverage, for skin substitutes, for delivery of viruses in gene therapy, for coating surgical implants (e.g., for coating an artificial pancreas) including coating vascular, e.g., cardiac, stents and for coating tissue culture plates for promoting cell adhesion and proliferation. As indicated above, various parameters may be varied to increase swelling ratios. Higher swelling ratios give faster drug release and are connected with high hydrophilicity which is important for contact lens and wound cleaning utilities, and provide better absorption for sanitary purposes. The hydrogels of the invention herein are useful, for example, for the controlled release of low molecular weight drugs, water-soluble macromolecules and proteins as well as for the scaffolds for tissue engineering.

We turn now to the alternative where a drug or biologic, e.g., of weight average molecular weight ranging from 200 to 1,000, is entrapped in a three dimensional network formed by free radical polymerization of (A) and (B) components of hydrogel-forming system herein. The model drug used in Example III herein is indomethacin which has potent gastrointestinal side effects following oral administration so a release system is important to it. Indomethacin is a nonsteroidal anti-inflammatory agent that has been widely used for treatment of rheumatoid arthritis, ankylosing spondylitis, osteoarthritis, acute painful shoulder, and acute gouty arthritis. Other drugs within this category, include, for example, flurbiprofen, proxyphylline, levamisole, and prednisolone. Still other drugs or biologics within this category include hypoestoxide, paclitaxel and other taxane derivatives, sirolimus, dexamethasone, trazolopyrimidine, tranilast, thalodomide and its analogs and simvastatin and other statin analogs. This alternative provides a good approach for controlled release administration of drugs.

We turn now to the alternative where a macromolecule, e.g., of weight average molecular weight ranging from 1,000 to 100,000, is entrapped in a three dimensional network formed by free radical polymerization of (A) and (B) components of hydrogel-forming system herein. The macromolecules can be water soluble and have, for example, a weight average molecular weight ranging from 1,000 to 10,000, or water insoluble and have, for example a weight average molecular weight ranging from 1,000 to 100,000. The water soluble macromolecules have a solubility in water of at least 0.1 mg/ml at 37° C. The water insoluble macromolecules have a solubility in water less than 0.1 mg/ml at 37° C. The macromolecules described in this paragraph exclude the polymers described in the next paragraph. The model macromolecule used in Example V herein is the polypeptide insulin. Other macromolecules for this alternative include, for example, trypsin-dallikrein inhibitor. Still other macromolecules for this alternative include antisense oligo nucleotides (e.g., antisense oligo nucleotide with morpholine based backbone which is sold under the name NEUGENES® which has limited water solubility), gene products (e.g., Ad5-FGF4 Gene for angiogenesis named GENERX® and described in Circulation, Mar. 19, 2002), two cell cycle inhibitory genes p27 and p16 as described in tctmd.com, Aug. 16, 2001, and antibodies and antibody fragments (e.g., c7E3 Fab denoted ABCIXIMAB® for antiplatelet use, described in Baron, J., et al, Cardiovascular Res 48, 464–472, 2000). This alternative provides a good approach for controlled release administration of macromolecule drugs.

We turn now the alternative where a synthetic or natural polymer, e.g., of weight average molecular weight ranging from 10,000 to 500,000, e.g., from 10,000 to 100,000, is entrapped in a three dimensional network formed by free radical polymerization of (A) and (B) components of hydrogel-forming system herein. The synthetic or natural polymers include, for example, proteins, peptides, polysaccharides, and polymucosaccharides. Proteins for this alternative include, for example, lysozyme, interleukin-1, and basic fibroblast growth factor. A model protein used in Example IV herein is bovine serum albumin. This alternative provides a good approach for controlled release administration of synthetic or natural polymer drugs.

For the three alternatives described above, entrapped component is readily incorporated by forming a solution of components (A) and (B) to provide a concentration of 30 to 50% (w/v) of total of (A) and (B) in the solution, adding photoinitiator and then adding, for example, from 0.5 to 3% (w/w based on the total weight of (A) and (B)) of agent to be entrapped, and then effecting free radical polymerization or by carrying out free radical polymerization in the presence of a suitable initiator without photoinitiator being present and photopolymerization being carried out. The solvent should be one in which (A) and (B), and agent to be entrapped are soluble and is, for example, an organic solvent. DMF is used in the examples. Other solvents in which (A) and (B) are soluble include, for example, dimethyl sulfoxide (DMSO), and selection is made from among the solvents in which (A) and (B) are soluble, to obtain solvent that also dissolves the agent to be entrapped. The solvent is readily removed by vacuum/heat or other solvent evaporization techniques. See O'Donnel, P. et al, Advance Drug Delivery Reviews 28, 25–42 (1997).

The hydrogels with agent entrapped therein are administered, e.g., by the method of administration used for the agent if that method is compatible with hydrogel use and are preferably administered orally (if this method is suitable for the agent). Administration is in dosages suitable to provide those associated with the agent, with controlled release being effected by the hydrogel.

We turn now to the third embodiment herein which is directed to a vascular stent, e.g., a cardiac stent, containing hydrogel containing entrapped agent where said agent is a therapeutic agent for treating, postponing or preventing disorder selected from the group consisting of coronary artery disease, inflammation, restenosis and stent rejection and is present in a therapeutically effective amount and the hydrogel containing entrapped agent is formed by the free radical polymerization of a hydrogel-forming system which comprises from 0.01 to 99.99% by weight of (A) a hydrophobic macromer with unsaturated group terminated ends, and from, 99.99 to 0.01% by weight of (B) a hydrophilic polymer which is a polysaccharide containing hydroxy groups which are reacted with unsaturated group introducing compound, the total of the percentages of (A) and (B) being 100%.

The hydrogel forming system is that described above in the first embodiment herein, and the hydrogel is that formed in the second embodiment herein. The therapeutic agent is selected from the group consisting of drugs or biologics of weight average molecular weight ranging from 200 to 1,000, macromolecules of weight average molecular weight ranging from 1,000 to 100,000 and synthetic or natural polymers of weight average molecular weight ranging from 10,000 to 500,000, that are functional for the purpose sought, that is for one or more of treating, postponing or preventing coronary artery disease, and/or inflammation and/or restenosis and/or stent rejection. Suitable therapeutic agents for the third embodiment herein include, for example, indomethacin, hypoestoxide, paclitaxel and other taxane derivatives, sirolimus, dexamethasone, trazolopyrimidine, tranilast, thaladomide and its analogs, simvastatin and other statin analogs, antisense oligo nucleotides (as described above, e.g., NEU-GENES®), Ad5-FGF4 Gene (GENERX®), the cell cycle inhibitory genes p27 and p16 and and antibodies and antibody fragments with antiplatelet effect (e.g., c7E3 Fab, ABCIXIMAB®).

The therapeutically effective amount of the therapeutic agent is that amount which accomplishes the purpose for which the therapeutic agent is present, e.g., an anti-inflammation effecting amount for an anti-inflammatory agent, a cholesterol reducing or HDL increase causing amount for an anti-cholesterol agent, a platelet formation inhibiting amount for an antiplatelet agent, a reocclusion ameliorating or preventing amount for agents administered for this purpose, an immune suppression effecting amount to prevent stent rejection and an angiogenesis causing amount for an angiogenesis promoting agent.

The hydrogel containing entrapped therapeutic agent can be attached directly onto a vascular stent or attached to a polymer coated vascular stent. The hydrogel containing entrapped agent can be used as a topcoat on a stent to provide a fast release, bolus-like localized administration of the entrapped agent. Under the hydrogel/therapeutic agent topcoating, other biodegradable polymer coatings (e.g., poly ester-amide with covalently conjugated or matrixed drugs) can be positioned to create a sustained release local drug/biologic delivery system.

A coating of hydrogel with drug entrapped therein can be formed on a vascular stent by forming a layer of solution of hydrogel forming system and therapeutic agent to be entrapped plus photoinitiator on the stent, then photopolymerizing and drying to form hydrogel on the stent. Alternatively a dry to the touch hydrogel with therapeutic agent entrapped there can be formed and this in turn can be attached to the stent with surgical adhesive or other bonding agent.

Embodiments of the invention herein are described and test results are set forth in U.S. Provisional Application No. 60/128,803, which is referred to above. The entire disclosure of U.S. Provisional Application No. 60/128,803, including Appendixes A, B, C and D thereof, is incorporated herein by reference.

The invention herein is illustrated by the following working examples.

EXAMPLE I

Poly-D,L-lactic acid (PDLLA), 5 gms, of weight average molecular weight of 800 was dissolved in tetrahydrofuran (concentration of 8% (w/v)) in a round-bottomed three-neck flask under nitrogen purge and the solution was cooled to 0° C. in an ice bath. Then 1.4 gms of 1,3-dicyclohexylcarbodiimide (DCC) and 0.9 gms 1-hydroxybenzotriazole (HOBT) were added (the mole ratio of DCC to PDLLA was 1:1 and the mole ratio of HOBT to PDLLA was 1:1), and reaction was conducted for 0.5 hours with continuous stirring. Then the mixture was allowed to reach room temperature whereupon 0.45 ml of 2-aminoethanol (mole ratio of 2-aminoethanol to PDLLA of 1.1:1) was added dropwise to the flask and stirring was then continued for 0.5 hours. The precipitated byproduct, cyclohexylurea salt, was filtered out. The diol product was obtained by pouring the filtrate into a large excess of dry hexane. It was further purified by dissolution and reprecipitation several times using tetrahydrofuran and hexane, respectively. Finally, the diol was dried in vacuo at room temperature for one day. The conversation of the —COOH end group to —OH group was 100%. The yield was more than 95%.

The diol, 4 gms, was dissolved in tetrahydrofuran (THF) in a flask to provide a concentration of 8% (gms/ml, w/v). The flask was flushed with nitrogen and chilled in an ice bath. Then 3 ml of triethylamine was added. After 5 minutes 1.8 ml of acryloyl chloride in THF (concentration of 30% (v/v)) was added to the flask dropwise. The mole ratio of triethylamine to diol was 4:1 and the mole ratio of acryloyl chloride to diol was 4:1. The mixture was stirred in an ice bath for three hours and then was reacted at room temperature for 18 hours. The diethanolamine hydrochloride byproduct was removed using a glass filter. The diacrylate product was precipitated using 10 times hexane. The product was further purified by dissolution and reprecipitation several times using THF and hexane respectively. The product was dried at room temperature under vacuum for one day and constituted the acryloyl derivative of the diol obtained from the poly-D,L-lactic acid, for use for macromer (A). The yield was around 90%.

Dextran, 2 gms, having a weight average molecular weight of 70,000, was added to a LiCl/DMF (4% w/v) solvent mixture. 3 gm LiCl in 80 ml DMF, inside a reaction flask which was maintained under continuous nitrogen gas flow. The flask was immersed in an oil bath and the temperature of the oil bath was raised from room temperature to 120° C. over a period of two hours and the resultant mixture became a homogenous gold colored solution. The solution was cooled down to room temperature and 2 ml pyridine (mole ratio of pyridine to anhydroglucose residue unit of dextran of 2:1) was added. After 5 minutes 2 ml acryloyl chloride (mole ratio of acryloyl chloride to anhydroglucose residue unit of dextran of 2:1) in DMF solution (concentration of 20% (v/v)) was slowly added to the flask with constant stirring. Reaction was then conducted at room temperature for three hours. Dextran acrylate was obtained by precipitating in an excess amount of cold ethanol. The product was filtered, washed with cold ethanol several times and dried at 40° C. under vacuum for two days. The product constituted the hydrophilic polymer (B). The product was found to have a degree of substitution (vinyl groups per hundred anhydroglucose units) of about 3.70.

The macromer (A) and the polymer (B) were dissolved in DMSO. Solutions of weight ratios of (B)/(A) of 90:10, 80:20, 70:30, 60:40 and 50:50 were made up by dissolving (A) and (B) in DMSO to obtain a final concentration of 30% w/v homogeneous solution. To each of the solutions was added 5% w/w (on the basis of the total weight of (A) and (B)) 2,2-dimethoxy 2-phenyl acetophenone. Each mixture was transferred to a hydrophobic PTFE plate and irradiated by a low-intensity, portable long wave length ultra violet lamp at room temperature for about 3 hours until a nontacky disk-shaped hydrogel was obtained (10 mm diameter, 1 mm thick). The hydrogels were extracted with deionized water and ethanol for 48 hours, respectively, to remove unreacted dextran diacrylate, unreacted poly-D,L-lactic acid derived diacrylate and DMSO solvent. The hydrogels were then dried in vacuo at 50° C. for 48 hours. Analysis indicated the formation of a crosslinked polymer network.

EXAMPLE II

Poly-D,L-lactic acid diacrylate to constitute the macromer (A) was obtained the same as in Example I.

Allyl isocyanate derivatized dextran was prepared as follows:

Dextran, 5 gms, having a weight average molecular weight of 43,000, was reacted with allyl isocyanate in the presence of dibutyltin dilaurate catalyst in a series of runs. In each of the runs, dry dextran was dissolved in anhydrous DMSO in a three-neck round bottom flask under a continuous nitrogen flow environment at room temperature. Then dibutyltin dilaurate (DBTDL) catalyst was injected into the solution at room temperature and then allyl isocyanate was added dropwise. In each case, the reaction mixture was stirred at a predetermined temperature for a predetermined time. Samples at different reaction times were withdrawn directly from the reaction flask with pipets. The resulting polymer samples were precipitated in cold excess isopropanol and were then further purified by dissolution and reprecipitating with DMSO and isopropanol respectively. The dex-AI products were dried at room temperature under reduced pressure for two days and stored in a cold (2° C.) dark place before being used for hydrogel formation.

The amounts of DBTBL and isocyanate, the reaction temperature, the reaction time and the degree of substitution (DS) obtained (number of allyl isocyanate groups per 100 anhydroglucose units) for the various runs are set forth in Table 1 below wherein reactants molar ratio means moles of DBTDL and moles of allyl isocyanate per anhydroglucose unit of glucose:

TABLE 1

| Samples | reactants molar ratio | | reaction temperature (° C.) | reaction time (hours) | DS |
|---|---|---|---|---|---|
| | DBTDL dextran | allyl isocyanate dextran | | | |
| Dex-AI-1 | 0.05 | 0.25 | room temp. | 2 | 0.95 |
| | | | | 4 | 1.72 |
| | | | | 6 | 2.31 |
| | | | | 8 | 3.13 |

TABLE 1-continued

| Samples | reactants molar ratio | | reaction temperature (° C.) | reaction time (hours) | DS |
|---|---|---|---|---|---|
| | DBTDL dextran | allyl isocyanate dextran | | | |
| Dex-AI-2 | 0.05 | 0.5 | room temp. | 2 | 1.81 |
| | | | | 4 | 2.06 |
| | | | | 6 | 2.78 |
| | | | | 8 | 3.49 |
| Dex-AI-3 | 0.1 | 1 | room temp. | 2 | 2.74 |
| | | | | 4 | 3.44 |
| | | | | 6 | 4.53 |
| | | | | 8 | 5.03 |
| Dex-AI-4 | 0.2 | 2 | room temp. | 2 | 3.86 |
| | | | | 4 | 4.87 |
| | | | | 6 | 6.92 |
| | | | | 8 | 9.04 |
| Dex-AI-5 | 0.08 | 1 | 45 | 6 | 8.36 |
| Dex-AI-6 | 0.1 | 1 | 45 | 2 | 7.81 |
| | | | | 4 | 9.54 |
| | | | | 6 | 11.27 |
| | | | | 8 | 12.94 |
| Dex-AI-7 | 0.1 | 1 | 60 | 2 | 9.25 |
| | | | | 4 | 10.93 |
| | | | | 6 | 12.38 |
| | | | | 8 | 14.14 |

Hydrogels were then made up using the diacrylate derived from poly-D,L-lactic acid (PDLLA diacrylate macromer) and dex-AI made the same as sample Dex-AI-3, 8 hours, in Table 1. Weight ratios of dex-AI to PDLLA diacrylate macromer of 90:10, 80:20, 70:30, 60:40, 50:50, 40:60, 30:70, 20:80 and 10:90 were made up within the scope of the invention. In each case, the dex-AI and PDLLA diacrylate macromer were dissolved in DMF to obtain a 50% (w/v) concentration solution. Five percent (w/w, based on total weight of dex-AI and PDLLA diacrylate macromer) of 2,2-dimethoxy 2-phenyl acetophenone initiator was added to the solution in each case. In each case, the resulting homogenous solution was transferred onto a hydrophobic PTFE plate and a disk shaped hydrogel was obtained by photocrosslinking the functionalized polymers at room temperature under a portable, long wave length ultra violet lamp as described in Example I. Finally, the hydrogels were dried in vacuo at 50° C. for 48 hours in a vacuum oven. FT-IR analysis performed with a Nicolet Magna 560 FT-IR spectrophotometer showed a crosslinked polymer network in each case.

EXAMPLE III

Indomethacin was used as a model drug to study release profiles of low molecular weight drugs from hydrogel prepared from hydrogel forming system herein. Indomethacin was particularly selected because it has potent gastrointestinal side effects following oral administration so a release system is important for it.

In this example, indomethacin was entrapped in hydrogels according to the invention (combinations of macromer (A) and polymer (B) over a range of composition ratios of (A) and (B)) and in hydrogels with only macromer (A) or polymer (B) and release in pH 7.4 phosphate buffered solution was investigated.

In a series of runs denoted the system 1 series of runs, the macromer (A) was PDLLA diacrylate macromer obtained from PDLLA (poly-D,L-lactic acid) having a weight average molecular weight of 800 and the polymer (B) was dex-AI where the dextran starting material had a weight average molecular weight of 43,000 and the dex-AI had a degree of substitution of 5.03.

In a series of runs denoted the system 2 series of runs, the macromer (A) was PDLLA diacrylate macromer obtained from PDLLA having a weight average molecular weight of 800 and the polymer (B) was dex-AI where the dextran starting material had a weight average molecular weight of 70,000 and the dex-AI had a degree of substitution of 6.77.

In a series of runs denoted the system 3 series of runs, the macromer (A) was PDLLA diacrylate macromer obtained from PDLLA having a weight average molecular weight of 7,000 and the polymer (B) was dex-AI where the dextran starting material had a weight average molecular weight of 70,000 and the dex-AI had a degree of substitution of 6.77.

The PDLLA diacrylate for the system 1 series of runs and for the system 2 series of runs was prepared the same as the PDLLA diacrylate of Example I. We turn now to the PDLLA diacrylate for the system 3 series of runs. The PDLLA diacrylate for the system 3 series of runs was prepared the same as the PDLLA diacrylate prepared in Example I, except that in preparing the diol, the PDLLA had a weight average molecular weight of 7,000, the mole ratio of DCC/PDLLA was 10:1, the mole ratio of HOBT/PDLLA was 10:1, the mole ratio of 2-aminoethanol/PDLLA was 10:1, reaction time at 0° C. was 2 hours and the reaction at room temperature was 4 hours, and except that in preparing the diacrylate from the diol, the mole ratio of triethylamine/PDLLA diol was 10:1, the mole ratio of acryloyl chloride/PDLLA diol was 10:1, the reaction time at 0° C. was 2 hours and the reaction time at room temperature was 48 hours.

The dex-AI for the system 1 series of runs was made up the same as the Dex-AI-3, 8 hours, of Table 1 of Example II. The dex-AI for the system 2 series of runs and for the system 3 series of runs was made up the same, and in each case the preparation was the same as for the Dex-AI-3, 8 hours, for the system 1 series of runs, except that dextran starting material of weight average molecular weight of 70,000 was used.

For the system 1 series of runs, hydrogels were made up with weight ratios of dex-AI/PDLLA diacrylate of 100/0, 80/20, 50/50, 20/80 and 0/100. For the system 2 series of runs, hydrogels were made up with weight ratios of dex-AI/PDLLA diacrylate of 100/0, 80/20, 50/50 and 20/80. For the system 3 series of runs, hydrogels were made up with weight ratios of dex-AI/PDLLA diacrylate of 80/20, 50/50, 20/80 and 0/100.

Thus, the percentages of the hydrophobic and hydrophilic components were varied as well as the molecular weights of the PDLLA and dextran starting materials.

Hydrogels were made up by dissolving PDLLA diacrylate macromer and dex-AI in DMF to provide a concentration of the total of the two in DMF of 50% w/v. Then 2,2-dimethoxy 2-phenyl acetophenone was added in each case as photoinitiator (5% w/w based on the total weight of PDLLA diacrylate macromer and dex-AI). Then directly before photo-crosslinking, 2.5% (w/w based on the total weight of PDLLA diacrylate macromer and dex-AI) indomethacin was added. The resulting compositions were transferred to PTFE plates and exposed to longwave UV light to form hydrogel discs of 8 mm diameter and 1 mm thickness, and the hydrogels were dried in vacuo at room temperature for several days.

Release of indomethacin from each of the hydrogels was determined by the following procedure. The experiments were carried out at 37° C. Each hydrogel was weighed and immersed in a glass vial containing 15 ml phosphate buffered solution (pH 7.4, 0.1 M) as a release medium. At time intervals over a course 1,000 hours, 2 ml samples were withdrawn from a sample and replaced by fresh buffer. The indomethacin concentration in a sample was determined by monitoring the absorbency of the medium at $\lambda=320$ on a Perkin Elmer Lambda 2 UV/VIS spectrometer and cumulative release versus time was determined from appropriate calculation; cumulative release was recorded as a percentage where the numerator for the calculation was the cumulative amount of indomethacin released by the time of sampling and the denominator was the maximum amount of indomethacin released. Results were as follows:

For all the hydrogels, indomethacin release appeared to be biphasic, i.e., an initial rapid release phase followed by a slower release phase.

Release of indomethacin from hydrogels where the dex-AI component was 100% continued for three to four days and finished before 120 hours and the molecular weight of the dextran starting material did not seem to have much effect on the release kinetics of the indomethacin.

Release of indomethacin from hydrogels where the PDLLA acrylate macromer component was 100% took about 750 hours for macromer made from PDLLA of molecular weight of 800 and 1,000 hours for macromer made from PDLLA of molecular weight of 7,000 so increase in molecular weight of the PDLLA caused decrease in release rate.

Turning now to the hydrogels prepared from both PDLLA diacrylate macromer and dex-AI components, release rate decreased with increase in weight percentage of PDLLA acrylate macromer component. The molecular weight of the dextran did not have much effect on the release rate of indomethacin for dex-AI dominant, e.g., 80% dex-AI/20% PDLLA diacrylate, hydrogels but the molecular weight of PDLLA was an important component of release rate in PDLLA acrylate dominant hydrogels (e.g., 20% dex-AI/80% PDLLA acrylate) as shown by slower release rates for 20% dex-AI/80% PDLLA acrylate hydrogels in the case of system 3 compositions (greater PDLLA molecular weight) than for system 2 composition.

Even small amounts of PDLLA acrylate were found to decrease swelling ratio and increase mechanical strength.

EXAMPLE IV

Bovine serum albumin was used as a model protein to study release profiles of proteins from hydrogel formed from hydrogel forming system herein. Bovine serum albumin was particularly selected because it is a well-characterized protein, large in size (weight average molecular weight of 69,000), easy to assay, low cost and generally available.

In this example, fluorescein isothiocyanate labeled bovine serum albumin (BSA) from Sigma Chemical was entrapped in hydrogels according to the invention (combinations of macromer (A) and polymer (B) over a range of composition ratios of (A) and (B)) and in hydrogels with only macromer (A) or polymer (B) and release in pH 7.4 phosphate buffered solution was investigated.

The hydrophobic macromer used was poly-D,L-lactic acid diacrylate (PDLLA diacrylate), made similarly to that in Examples I and II, starting with poly-D,L-lactic acid of weight average molecular weight of 740 (supplied by Boehringer Ingelheim Chemicals).

The hydrophilic polymer used was dex-AI, made similarly to those in Example II, starting with dextran having a weight average molecular weight of 43,000 (purchased from Sigma Chemical Company) and had a degree of substitution (number of allyl isocyanate groups per 100 anhydroglucose units) of 6.

Hydrogels were made up by dissolving PDLLA diacrylate macromer and dex-AI in DMF to provide a concentration of the total of the two in DMF of 50% w/v. Then 2,2-dimethoxy 2-phenyl acetophenone was added in each case as photoinitiator (2.5% w/w based on the total weight of PDLLA diacrylate macromer and dex-AI). Then directly before photocrosslinking, 2.5% (w/w based on the total weight of PDLLA diacrylate macromer and dex-AI) of the BSA was added. The resulting compositions were transferred to PTFE plates and exposed to longwave UV light (8 watts, 365 nm) for 3 hours to form hydrogel discs of 8 mm diameter and 1 mm thickness, and the formed hydrogels with BSA entrapped therein were dried in vacuo at room temperature for several days until a constant weight was reached. Hydrogels were made up with weight ratios of dex-AI/PDLLA diacrylate of 100/0, 80/20, 50/50, 20/80 and 0/100.

Release of BSA was determined by the following procedure. In each case, about 35 mg hydrogel was placed inside a 20 ml screw capped glass test tube containing 15 ml phosphate-buffered solution (PBS) (0.1 M, pH 7.4). The test tubes were placed in a 37° C. incubator. At predetermined intervals over a course of 60 days, 2 ml liquid samples were drawn and replaced by fresh PBS. The concentration of BSA in each withdrawn sample was measured at 490 nm using a Perkin Elmer Lambda 2 UV/VIS spectrometer (Norwalk, Conn.). All release studies were carried out in triplicate.

All the release profiles were characterized by an initial burst release during the first two days followed by a sustained release. The total amount of release of BSA from the 100% dex-AI hydrogel reached 62% after 58 days, and 30% of this total amount was released during the first two days incubation. The 100% PDLLA diacrylate hydrogel provided a release profile with 13% burst effect during the first two days incubation and all the BSA was released by around 48 days of incubation. With hydrogels from both dex-AI and PDLLA diacrylate, the initial burst release decreased significantly compared to the 100% dex-AI hydrogel. For example, only 10% of the BSA released from the 80/20 dex-AI/PDLLA diacrylate hydrogel during the first two days incubation, 16% for 50/50, and 15% for 20/80 dex-AI/PDLLA diacrylate. Hydrogels from both dex-AI and PDLLA diacrylate did not release all the BSA by the end of the 60-day period. The total amounts of BSA released during the 60-day study were found to be 49% for 80/20, 64% for 50/50, and 98% for 20/80 dex-AI/PDLLA diacrylate. Generally, the release rate of BSA from dex-AI/PDLLA diacrylate hydrogels increased as PDLLA diacrylate component percentage of dex-AI plus PDLLA diacrylate, increased.

The release of BSA from the dex-AI/PDLLA diacrylate hydrogels was both diffusion and degradation controlled. During the initial burst phase, the hydrophilicity of dex-AI was a major reason for microporous structure formation, which was responsible for the diffusion controlled release. Thereafter as PDLLA diacrylate hydrolytic degradation proceeded, BSA release was degradation controlled.

The data showed that the combination of the hydrophobic hydrolytic degradable PDLLA diacrylate and hydrophilic non-hydrolytic degradable dex-AI reduces the initial burst effect compared to the result from the 100% dex-AI hydrogel and prolonged the release duration of BSA compared to the results from the 100% PDLLA diacrylate hydrogel.

EXAMPLE V

Insulin, a polypeptide, was used as a model water-soluble macromolecule to study release profiles of these from hydrogel formed from hydrogel forming system herein.

In this example, fluorescein isothiocyanate labeled insulin (weight average molecular weight of 6,000), i.e., FITC-insulin, from Sigma Chemical was entrapped in hydrogels according to the invention (combinations of macromer (A) and polymer (B) over a range of composition ratios of (A) and (B)) and in hydrogels with only macromer (A) or polymer (B) and release in pH 7.4 phosphate buffered solution was investigated.

The hydrophobic macromer used was poly-D,L-lactic acid diacrylate (PDLLA diacrylate) made similarly to that in Examples I and II, starting with poly-D,L-lactic acid of weight average molecular weight of 740 (supplied by Boehringer Ingelheim Chemicals).

The hydrophilic polymer was dex-AI, made similarly to those in Example II, starting with dextran having a weight average molecular weight of 43,000 (purchased from Sigma Chemical Company) and had a degree of substitution (number of allyl isocyanate groups per 100 anhydroglucose units) of 6.

Hydrogels were made up by dissolving PDLLA diacrylate macromer and dex-AI in DMF to provide a concentration of the total of the two in DMF of 50% (w/v). Then 2,2-dimethoxy-2-phenyl acetophenone was added in each case as photoinitiator (2.5% w/w based on the total weight of PDLLA diacrylate macromer and dex-AI). Then 2.5% (w/w based on the total weight of PDLLA diacrylate macromer and dex-AI) of the labeled insulin was added to the solution. The resulting solutions were transferred onto hydrophobic PTFE plates and disc-shaped hydrogels were obtained by crosslinking the unsaturated functional groups of dex-AI and PDLLA diacrylate under a portable long wavelength ultra-violet lamp (8 watts, 365 nm) at room temperature for 3 hours. The labeled insulin-incorporated hydrogels were dried under vacuum at room temperature for several days to remove residual solvent. Hydrogel disks of 8 mm diameter and 0.8 mm thickness were formed. Hydrogels were made up with weight ratios of dex-AI/PDLLA diacrylate of 100/0, 80/20, 50/50, 20/80 and 0/100.

Release of insulin was determined by the following procedure. In each case, about 35 mg labeled insulin-incorporated hydrogel was placed in a 20 ml screw capped glass test tube containing 15 ml phosphate buffered solution (PBS, 0.1 M, pH 7.4) at 37° C. and immersed therein over a period of seven weeks. 2 ml of the buffer medium was removed at predetermined intervals and replaced with the same volume of fresh buffer solution. The concentration of insulin in each withdrawn sample was measured at 490 nm using a Perkin Elmer Lambda 2 UV/VIS spectrometer (Norwalk, Conn.). An average release of three samples was reported (i.e., tests were carried out in triplicate and results were averaged).

The results were as follows: The initial burst from a 100% dex-AI hydrogel was minimal. However, as the percentage of PDLLA diacrylate increased, initial burst, release extent, and release rate increased. The 100% PDLLA diacrylate hydrogel showed the largest initial burst effect, highest release extent, and highest release rate. For example, only 14% entrapped insulin was released from the 100% dex-AI hydrogel after seven weeks incubation. The release extent increased as percentage of PDLLA diacrylate component increased, i.e., 32% for 80/20, 60% for 50/50, 72% for 20/80 dex-AI/PDLLA diacrylate, and 100% of the insulin was released from the 100% PDLLA diacrylate hydrogel by about 44 days. The release rates were largest at the beginning of the immersion period.

Figure 1A:
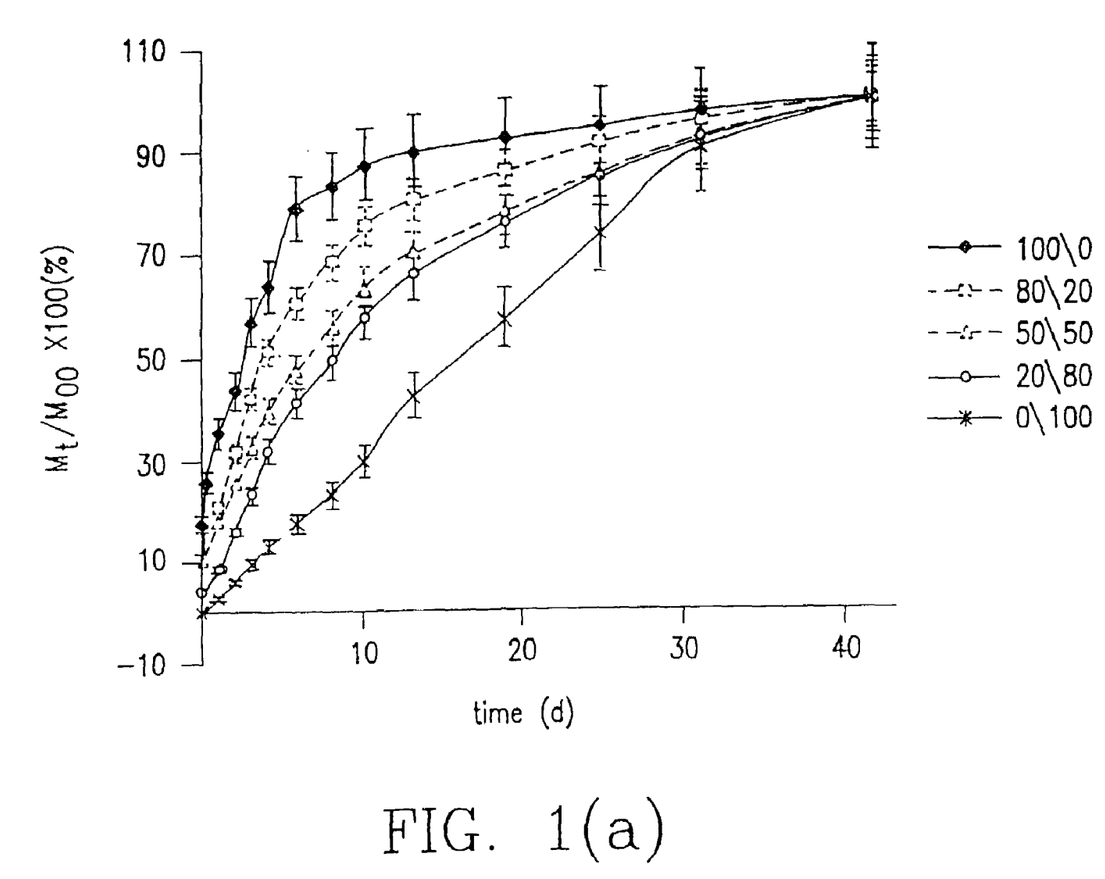
FIGS. 1a, 1b, and 1c are graphs of cumulative release versus time respectively for indomethacin (IDM), insulin, and bovine serum albumin (BSA) and are referred to in Example V hereinafter.
Figure 1B:
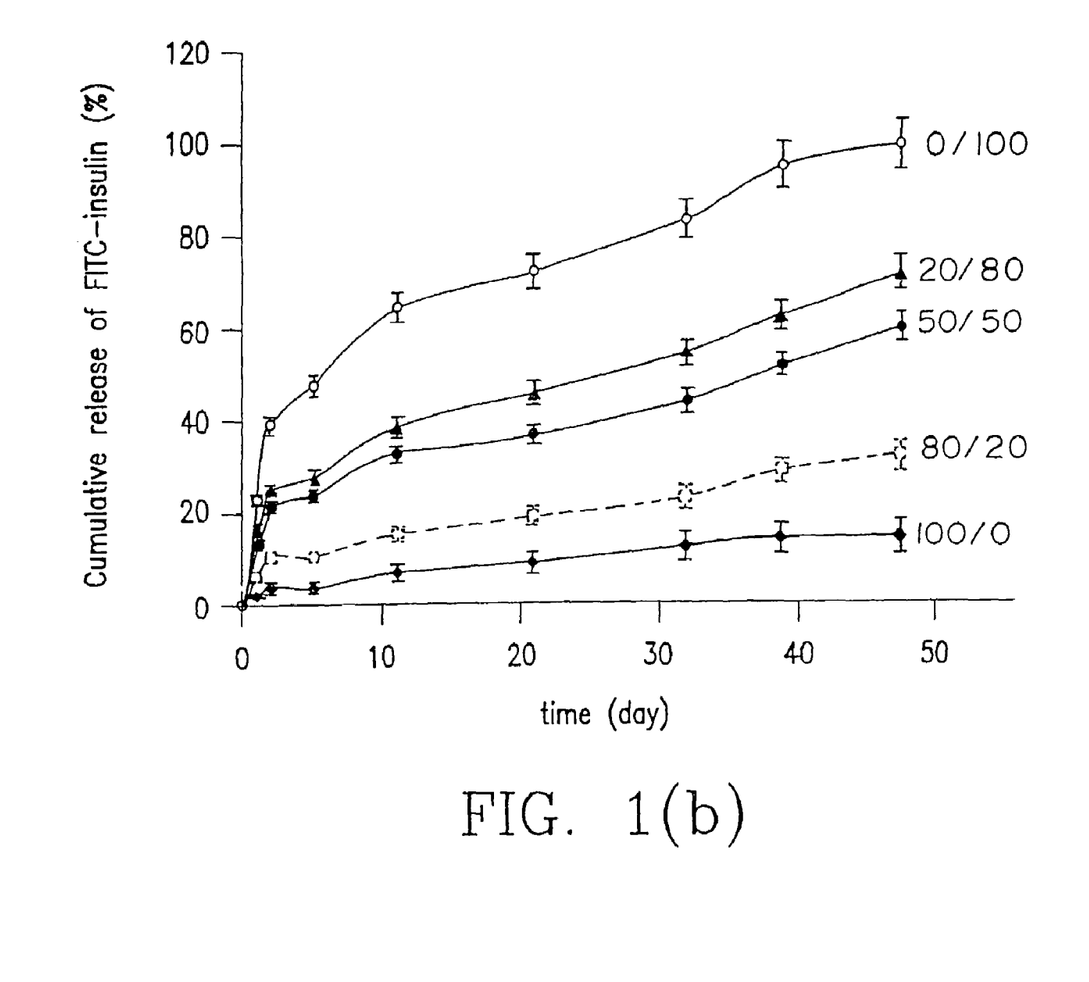
Figure 1C:
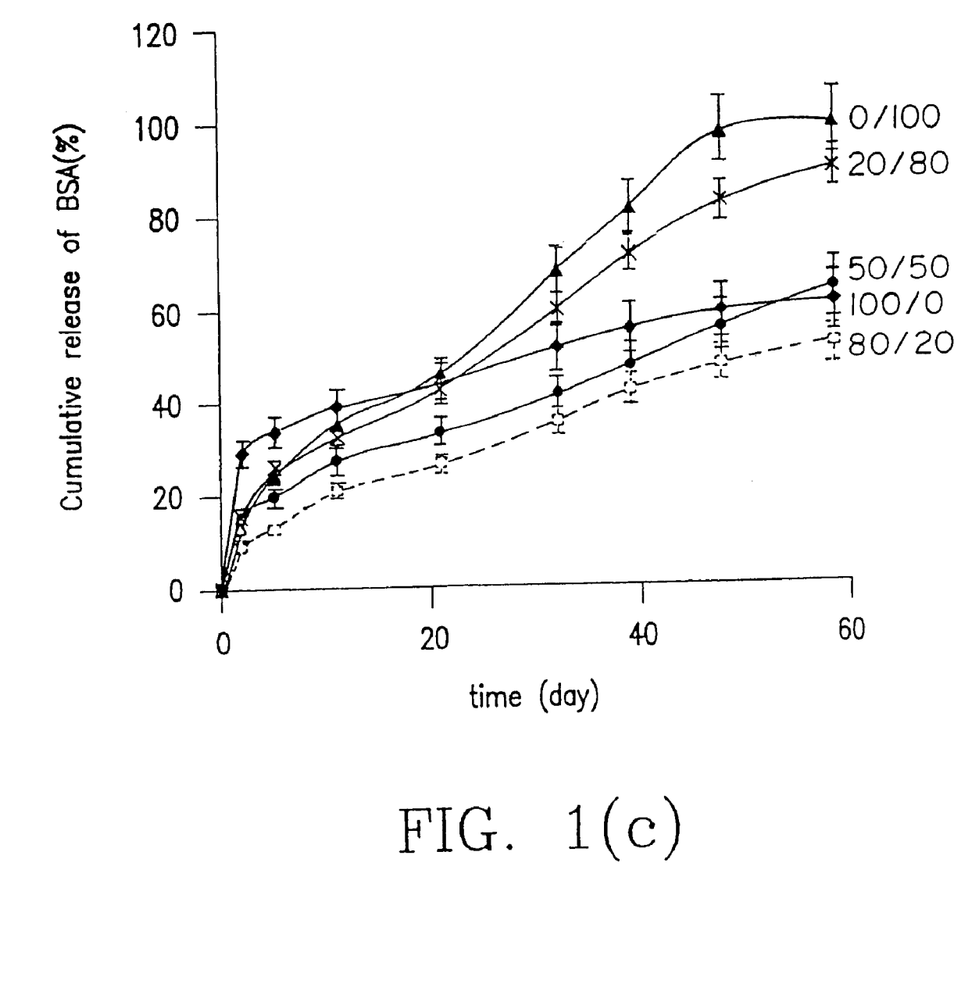

The results for indomethacin incorporated 100/0, 80/20, 50/50, 20/80 and 0/100 weight ratio, for insulin-incorporated 100/0, 80/20, 50/50, 20/80 and 0/100 weight ratio, and for BSA-incorporated 100/0, 50/50, 80/20, 20/80 and 0/100 weight ratio dex-AI/PDLLA diacrylate hydrogels are shown respectively in FIGS. 1a, 1b, and 1c. As shown in FIG. 1a, the small size indomethacin could be totally released from all the hydrogels within 40 days, and the release rate decreased as PDLLA diacrylate component percentage increased. As shown in FIGS. 1b and 1c, release rate of the larger size molecules insulin and BSA increased as PDLLA diacrylate component percentage increased, and the large size molecules were not totally released from the high dex-AI component hydrogels such as 100/0 and 80/20 within the period of the experiments. The effect of dex-AI/PDLLA diacrylate composition ratio on the release profiles of large molecules such as proteins represented by BSA and smaller water soluble macromolecules as represented by insulin are shown to be different. Generally, the BSA initial burst release decreased as percentage of PDLLA diacrylate component increased, and thereafter as immersion time increased, there was a sustained release, the rate and extent of which increased as percentage of PDLLA diacrylate increased. On the other hand, insulin release is shown to increase during the entire period (including initially) as percentage of PDLLA diacrylate component increased. In all cases, the hydrogel networks provided controlled release of the entrapped agent.

EXAMPLE VI

A solution of PDLLA diacrylate macromer and dex-AI in DMF is made up as in Example III for the system 3 composition with 20% dex-AI/80% PDLLA diacrylate (total concentration of the two in DMF of 50% w/v). Then 2,2-dimethoxy 2-phenyl acetophenone is added as photoinitiator (5%, w/w based on total weight of PDLLA diacrylate macromer and dex-AI). Then directly before coating, 2.5% (w/w based on the total weight of PDLLA diacrylate macromer and dex-AI) indomethacin, is added. The resulting composition is directly coated on a vascular stent whereupon the coated stent is exposed to UV light to form hydrogel with indomethacin entrapped therein on the stent in a layer of 1 mm thickness whereupon drying is carried out at room temperature until a stent coated with a layer of hydrogel with indomethacin entrapped therein that is dry to the touch, is formed. The coated stent deployed after angioplasty is associated with reduced inflammation compared to a conventional stent.

VARIATIONS

Many variations of the above will be obvious to those skilled in the art. Thus, the invention is defined by the claims.

What is claimed is:

1. Hydrogel-forming system which comprises hydrophobic and hydrophilic components (A) and (B) which are convertible into a one phase crosslinked network structure by free radical polymerization, where the hydrophobic and hydrophilic components constitute different compounds from one another, the hydrophobic component (A) being a hydrophobic macromer with unsaturated group terminated ends, and the hydrophilic component (B) being a hydrophilic polymer which is a polysaccharide containing hydroxy groups which are reacted with unsaturated group introducing compound, the hydrogel-forming system comprising from 0.01 to 99.99% by weight of (A) and from 99.99 to 0.01% (B), with the total of the percentages of (A) and (B) leaving 100%.

2. The hydrogel-forming system of claim 1 where the hydrophobic macromer is made from aliphatic polyester starting material.

3. The hydrogel-forming system of claim 1 where the hydrophobic macromer is made from poly (lactic acid) starting material.

* * * * *